(12) United States Patent
Schmidt et al.

(10) Patent No.: US 8,612,167 B2
(45) Date of Patent: Dec. 17, 2013

(54) ESTIMATING REMAINING BATTERY SERVICE LIFE IN AN IMPLANTABLE MEDICAL DEVICE

(75) Inventors: Craig L. Schmidt, Eagan, MN (US); John D. Wahlstrand, Shoreview, MN (US); Ann M. Crespi, Mobile, AL (US); Gregory A. Younker, White Bear Township, MN (US); James W. Busacker, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 12/743,394

(22) PCT Filed: Jan. 18, 2008

(86) PCT No.: PCT/US2008/051445
§ 371 (c)(1),
(2), (4) Date: Nov. 5, 2010

(87) PCT Pub. No.: WO2009/091407
PCT Pub. Date: Jul. 23, 2009

(65) Prior Publication Data
US 2011/0130984 A1 Jun. 2, 2011

Related U.S. Application Data

(60) Provisional application No. 61/190,068, filed on Jan. 18, 2007.

(51) Int. Cl.
*G01R 31/36* (2006.01)
*G01R 19/00* (2006.01)
*A61N 1/00* (2006.01)
*H02J 7/00* (2006.01)

(52) U.S. Cl.
USPC .............. 702/63; 702/64; 607/29; 320/136

(58) Field of Classification Search
USPC .............. 702/63, 60, 64; 607/29, 27, 28, 9; 429/90, 92; 320/127, 132
See application file for complete search history.

(56) References Cited

U.S. PATENT DOCUMENTS

| 4,259,639 A | 3/1981 | Renirie |
| 4,290,429 A | 9/1981 | Blaser |

(Continued)

FOREIGN PATENT DOCUMENTS

| WO | 9501205 A1 | 1/1995 |
| WO | 0024459 A1 | 5/2000 |

(Continued)

*Primary Examiner* — Marc Armand
*Assistant Examiner* — Ricky Ngon
(74) *Attorney, Agent, or Firm* — Carol F. Barry (57) ABSTRACT

Methods for estimating a remaining service life of an implantable medical device (IMD) battery are presented. In one embodiment, a characteristic discharge model of the battery is employed. Systems employing the methods may include an external device coupled to the IMD, for example, via a telemetry communications link, wherein a first portion of a computer readable medium included in the IMD is programmed to provide instructions for the measurement, or tracking, of time and the measurement of battery voltage, and a second portion of the computer readable medium included in the external device is programmed to provide instructions for carrying out the calculations when the voltage and time data is transferred via telemetry from the IMD to the external device.

30 Claims, 8 Drawing Sheets

(56) References Cited

U.S. PATENT DOCUMENTS

| | | | |
|---|---|---|---|
| 4,448,197 A | 5/1984 | Nappholz et al. | |
| 4,715,381 A | 12/1987 | Moberg | |
| 5,391,193 A | 2/1995 | Thompson | |
| 5,402,070 A | 3/1995 | Shelton et al. | |
| 6,108,579 A | 8/2000 | Snell et al. | |
| 6,148,235 A | 11/2000 | Kuiper | |
| 6,671,552 B2 | 12/2003 | Merritt et al. | |
| 7,711,426 B2* | 5/2010 | Armstrong et al. | 607/29 |
| 7,877,145 B2* | 1/2011 | Russie | 607/31 |
| 7,941,220 B2* | 5/2011 | Tobacman | 607/29 |
| 2002/0140399 A1 | 10/2002 | Echarri et al. | |
| 2003/0065366 A1 | 4/2003 | Merritt et al. | |
| 2004/0039424 A1* | 2/2004 | Merritt et al. | 607/29 |
| 2005/0177206 A1 | 8/2005 | North et al. | |
| 2005/0277994 A1 | 12/2005 | McNamee et al. | |
| 2006/0025828 A1 | 2/2006 | Armstrong et al. | |
| 2006/0149220 A1 | 7/2006 | Ullestad et al. | |
| 2009/0273313 A1 | 11/2009 | Scott et al. | |

FOREIGN PATENT DOCUMENTS

| | | |
|---|---|---|
| WO | 0108749 A1 | 2/2001 |
| WO | 2005110515 A1 | 11/2005 |
| WO | 2008121109 A1 | 10/2008 |
| WO | 2009134471 A1 | 11/2009 |

\* cited by examiner

$$mV = (a_{1i} + a_{1z}\ln(j)) + \frac{(b_{1i} + b_{1z}\ln(j))}{1 + \exp(-\frac{\%U - (c_{1i} + c_{1z}\ln(j))}{(d_{1i} + d_{1z}\ln(j))})} + \frac{(a_{2i} - a_{2z}\ln(j))}{1 + \exp(-\frac{\%U - (b_{2i} + b_{2z}\ln(j))}{(c_{2i} + c_{2z}\ln(j))})} +$$

$$\frac{(b_{3i} + b_{3z}\ln(j))}{1 + \exp(-\frac{\%U - (c_{3i} + c_{3z}\ln(j))}{(d_{3i} + d_{3z}\ln(j))})} + \frac{(b_{4i} + b_{4z}\ln(j))}{1 + \exp(-\frac{\%U - (c_{4i} + c_{4z}\ln(j))}{(d_{4i} - d_{4z}\ln(j))})} + \frac{1}{(a_{5i} - a_{5z}\ln(j)) + (b_{5i} + b_{5z}\ln(j)) * \%U}$$

| DOD | 10 uA Min | 10 uA Max | 10 uA Range | 15 uA Min | 15 uA Max | 15 uA Range | 20 uA Min | 20 uA Max | 20 uA Range | 30 uA Min | 30 uA Max | 30 uA Range | 40 uA Min | 40 uA Max | 40 uA Range | 60 uA Min | 60 uA Max | 60 uA Range | 80 uA Min | 80 uA Max | 80 uA Range |
|---|---|---|---|---|---|---|---|---|---|---|---|---|---|---|---|---|---|---|---|---|---|
| 10 | 85.1 | 155.3 | 70.2 | 54.6 | 104.2 | 49.5 | 39.6 | 76.0 | 36.4 | 27.6 | 49.8 | 22.2 | 20.3 | 36.6 | 16.3 | 13.5 | 24.9 | 11.4 | 10.0 | 16.7 | 6.7 |
| 20 | 72.5 | 141.0 | 68.4 | 46.4 | 94.6 | 48.2 | 33.5 | 68.7 | 35.2 | 23.4 | 44.8 | 21.4 | 17.1 | 33.2 | 16.1 | 11.4 | 22.4 | 10.9 | 8.5 | 16.9 | 6.3 |
| 30 | 62.5 | 121.9 | 59.3 | 40.7 | 81.6 | 40.9 | 29.4 | 59.3 | 29.9 | 20.2 | 38.7 | 18.5 | 14.4 | 28.7 | 13.3 | 10.2 | 19.2 | 9.3 | 7.4 | 14.4 | 7.0 |
| 40 | 58.0 | 99.3 | 41.3 | 37.0 | 66.4 | 29.4 | 26.8 | 48.0 | 21.3 | 18.0 | 31.4 | 13.4 | 13.5 | 23.4 | 10.2 | 8.9 | 15.5 | 6.6 | 6.9 | 11.6 | 5.0 |
| 50 | 52.3 | 74.9 | 22.6 | 33.9 | 49.6 | 15.7 | 24.7 | 35.7 | 11.0 | 16.0 | 23.5 | 7.5 | 11.7 | 17.7 | 5.9 | 7.8 | 11.5 | 3.9 | 5.5 | 8.8 | 3.3 |
| 60 | 41.2 | 53.9 | 12.8 | 27.0 | 35.1 | 8.1 | 19.4 | 25.6 | 6.3 | 12.5 | 16.5 | 3.9 | 9.3 | 12.3 | 3.0 | 6.1 | 7.9 | 1.9 | 4.4 | 5.8 | 1.4 |
| 70 | 27.8 | 38.5 | 10.7 | 17.4 | 24.8 | 7.4 | 12.3 | 17.7 | 5.4 | 8.0 | 11.8 | 3.8 | 5.8 | 8.8 | 2.8 | 3.6 | 5.3 | 1.5 | 2.8 | 3.8 | 1.0 |
| 80 | 15.9 | 22.2 | 6.3 | 9.8 | 13.8 | 3.9 | 6.5 | 9.5 | 3.1 | 4.0 | 6.2 | 2.3 | 2.7 | 4.8 | 2.1 | 1.1 | 3.0 | 1.9 | 1.0 | 2.1 | 1.1 |
| 85 | 9.5 | 15.4 | 6.1 | 4.6 | 10.2 | 5.4 | 2.4 | 7.3 | 4.9 | 1.2 | 4.5 | 3.2 | 0.8 | 3.4 | 2.6 | 0.5 | 1.9 | 1.5 | 0.1 | 1.2 | 1.1 |
| 90 | 2.1 | 8.2 | 6.2 | 0.8 | 3.9 | 3.1 | -0.1 | 1.7 | 1.8 | -0.3 | 1.0 | 1.3 | -0.5 | 0.7 | 1.2 | -0.6 | 0.3 | 0.9 | -0.6 | 0.1 | 0.7 |
| 95 | -3.9 | 0.4 | 4.3 | -3.4 | -1.0 | 2.4 | -3.2 | -2.0 | 1.2 | -2.3 | -1.0 | 0.7 | -1.8 | -1.3 | 0.7 | -1.5 | -1.2 | 0.4 | -1.3 | -1.0 | 0.3 |

ESTIMATING REMAINING BATTERY SERVICE LIFE IN AN IMPLANTABLE MEDICAL DEVICE

RELATED APPLICATIONS

The present application claims the benefits of U.S. Provisional Patent Application Ser. No. 61/190,068, having a filing date of Jan. 18, 2007, which resulted from conversion of U.S. patent application Ser. No. 11/624,254 filed Jan. 18, 2007, and requested to be converted to a provisional application on Jan. 18, 2008, the disclosure of which is incorporated herein by reference in its entirety.

TECHNICAL FIELD

The present invention pertains to implantable medical devices (IMDs) and more particularly to systems and methods for estimating the remaining service life of an IMD battery.

BACKGROUND

A number of commercially available programmable IMDs, for example, cardiac pacemakers and defibrillators, electrical signal monitors, hemodynamic monitors, nerve and muscle stimulators and infusion pumps, include electronic circuitry and a battery to energize the circuitry for the delivery of therapy and/or for taking physiological measurements for diagnostic purposes. It is common practice to monitor battery life within an IMD so that a patient in whom the IMD is implanted should not suffer the termination of therapy, and or diagnostic benefit, from that IMD when the IMD battery runs down. Several methods for deriving estimates of remaining battery life, which employ monitoring schemes that require periodic measurements of battery voltage and either, or both of, battery impedance and current drain, have been described in the art, for example, in commonly assigned U.S. Pat. No. 6,671,552. Although the previously described methods can provide fairly accurate estimates of remaining battery life, there is still a need for methods that employ simplified monitoring schemes in which fewer measurements are taken.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 6 is a chart including an exemplary array of times defining remaining battery service life;

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Figure 1:
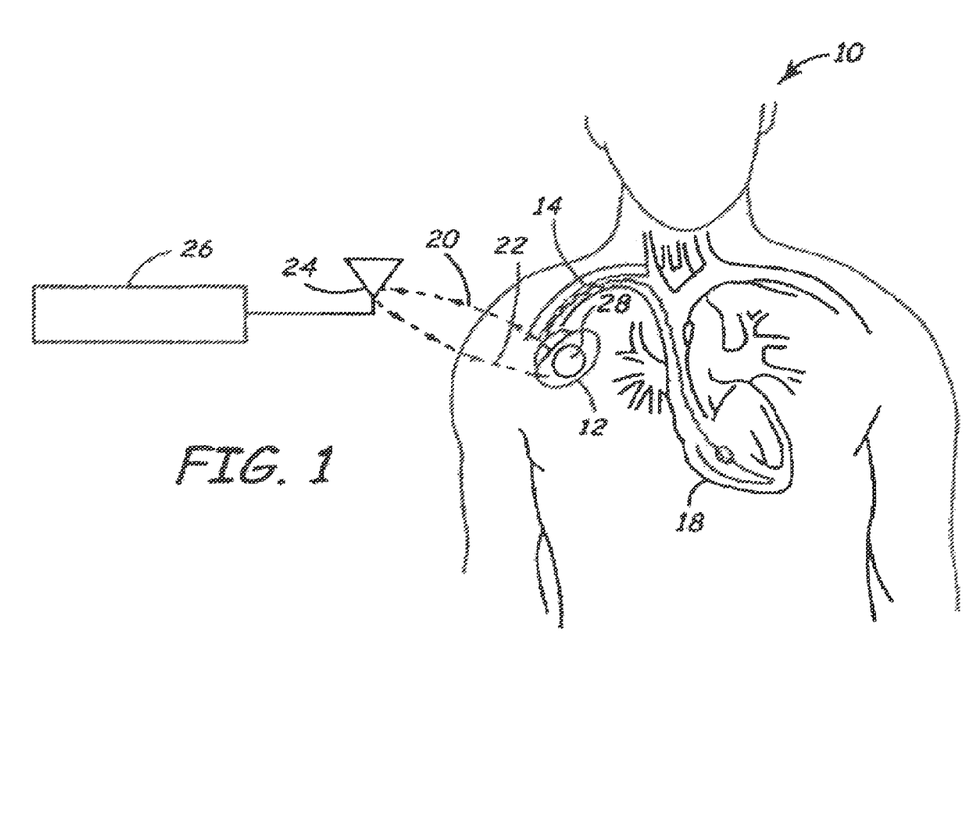
FIG. 1 is a schematic of an exemplary system in which embodiments of the present invention may be employed.
Figure 2:
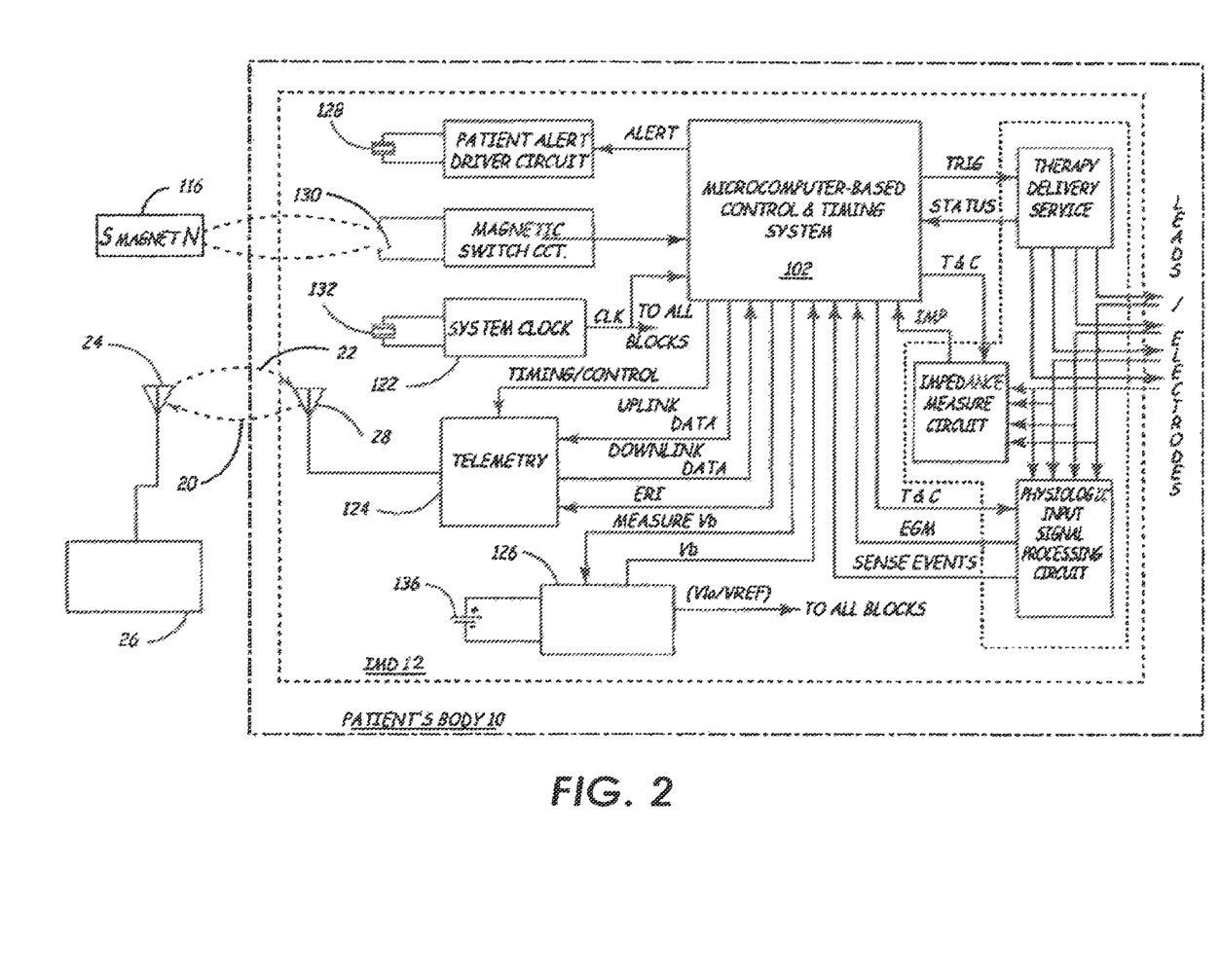
FIG. 2 is a block diagram of an exemplary system architecture.

FIG. 1 is a schematic of an exemplary system in which embodiments of the present invention may be employed. FIG. 1 illustrates an IMD 12 and an endocardial lead 14 implanted within a patient 10. Lead 14 electrically couples IMD 12 to a heart 18 of patient 10 in order that therapy, for example, pacing pulses, may be delivered from IMD 12 to heart 18. FIG. 2 is a block diagram of an exemplary system architecture of IMD 12 for initiating and controlling pacing therapy delivery, for processing physiological signals sensed by lead 14, and for initiating and tracking device-related measurements. The exemplary system is described in greater detail in the aforementioned commonly assigned U.S. Pat. No. 6,671,552, salient portions of which are hereby incorporated by reference. The scope of the present invention is not limited to the type of therapy delivered. For example, IMD 12 may be implanted in a different location than that shown in FIG. 1 and/or may include additional or alternate components for providing additional or alternate therapies, for example, an infusion pump for delivery of therapeutic agents, and/or a capacitor and associated high voltage circuitry for delivery of defibrillation pulses. Furthermore, embodiments of the present invention may be employed by systems including IMDs that only function as monitors, for example, electrocardiography and hemodynamic monitors.

FIG. 2 illustrates IMD 12 including a battery 136 coupled to power supply circuitry 126 for powering the operation of IMD 12. Circuitry 126 is also shown controlled by a microcomputer-based system 102 to measure battery voltage and return a value for each measured voltage. In addition to providing control and timing for the function of IMD 12, system 102 includes means for storing sensed physiologic parameters as well as device specific data. According to embodiments of the present invention, system 102 is pre-programmed to measure battery voltage at particular points in time after an initial measurement is made when IMD 12 is implanted in patient 10. Time from implant is tracked by IMD 12, for example, by a piezoelectric crystal 132 coupled to a system clock 122, according to the illustrated embodiment, so that each battery voltage measurement is stored in memory with an associated time. Each point in time may be a range of seconds in duration, for example, up to about 10 seconds, in which case each associated voltage measurement is actually an average over the range of seconds.

FIGS. 1 and 2 further illustrate IMD 12 including a telemetry antenna 28 coupled to telemetry circuitry 124, which is controlled by system 102 and receives and transmits data therefrom and thereto. Antenna 28 may be coupled by a telemetry communications link to an external telemetry antenna 24 of an external device 26, to facilitate uplink and downlink data transmissions 20, 22 between IMD 12 and external device 26, which may be activated by closure of a magnetic switch 130 by an external magnet 116. Other communication interfaces may also be incorporated. External device 26 may perform as both a monitor and programmer for IMD 12, or just as a monitor. Exemplary telemetry transmission schemes and associated components/circuitry for systems may be included in IMDs.

At the time of implant and/or at subsequent check-ups, a clinician uplinks each stored battery voltage measurement and its associated time of measurement, via telemetry, to external device 26, which includes pre-programmed instructions for using the voltage and time data in performing iterative calculations and/or determination to estimate time of remaining service life of battery 136. Alternately, system 102 may be pre-programmed with the instructions to perform the calculations and/or determinations to estimated remaining service life, which estimated remaining life may be uplinked to external device 26 for display. Methods of the present invention for determining the estimated remaining battery service life rely upon a known characteristic discharge model for the battery, in conjunction with tracked time since implant, and will be described in greater detail below.

Figure 3:
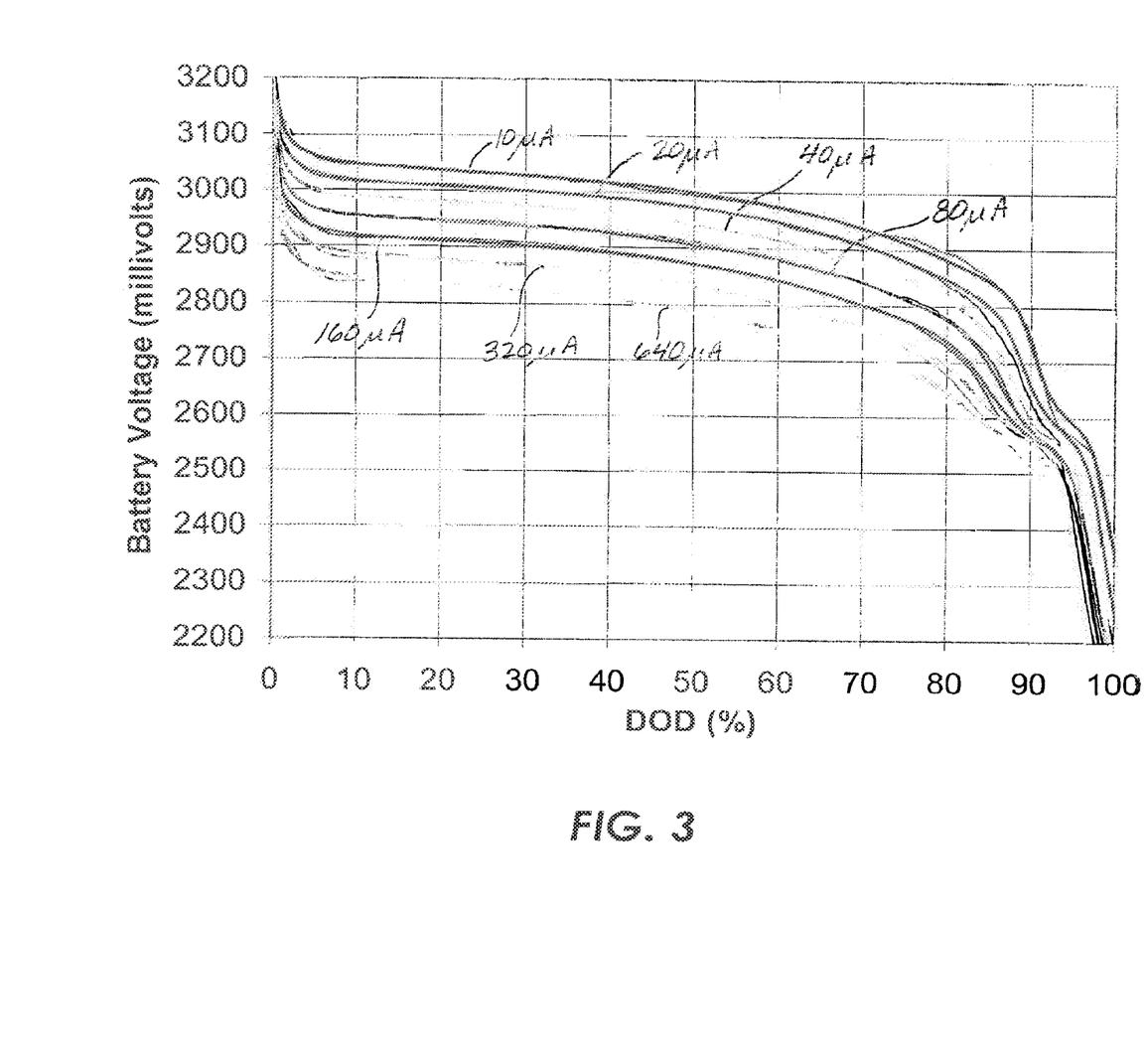
FIG. 3 is an exemplary hybrid cathode discharge model of battery voltage versus depth of discharge for various current drains.
Figure 4:
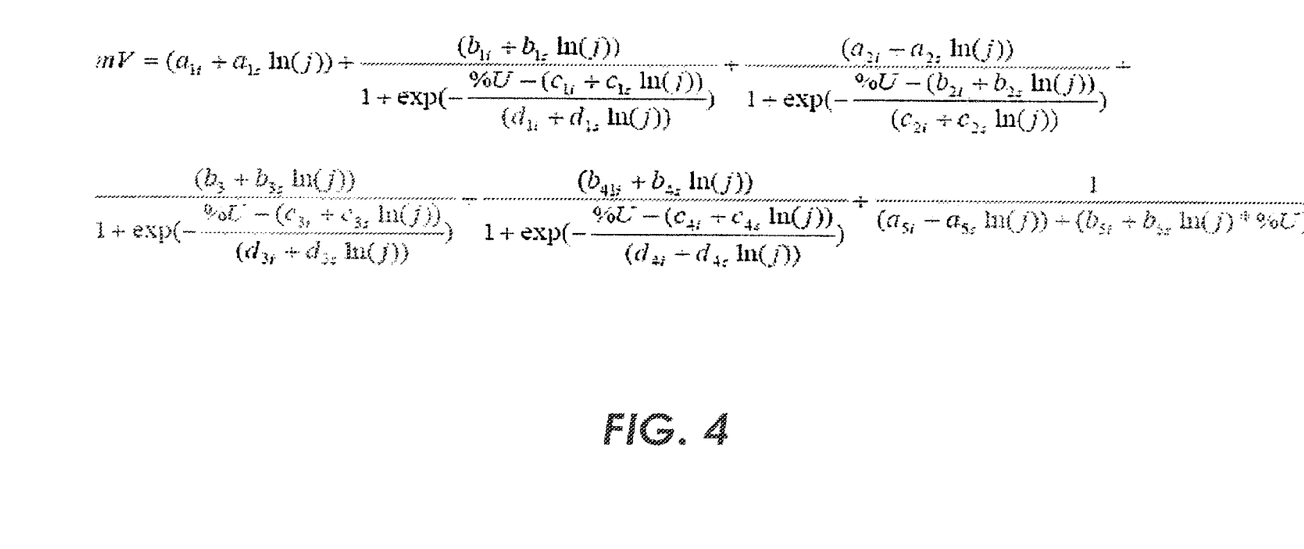
FIG. 4 is an equation defining the discharge model, from which the plots of FIG. 2 may be derived.

FIG. 3 is a representation of an exemplary hybrid cathode discharge model, which is plotted as battery voltage versus depth of discharge for various current drains, according to exemplary embodiments of the present invention. FIG. 4 is an equation defining the discharge model from which the plots of FIG. 3 may be derived. According to exemplary embodiments of the present invention, battery 136 is a lithium carbon fluoride (also referred to as carbon monofluoride or poly(carbon monofluoride))-silver vanadium oxide (where C refers to SVO made by combinational method) (Li/CF$_x$-CSVO) battery having a lithium anode, a cathode comprising about 27% by weight (wt.) CSVO, about 63% by wt. CF$_x$, about 7% by wt. PTFE, and about 3% by wt. carbon black, and an electrolyte of 1 M LiBF$_4$ in a blend of about 60 volume percent (vol %) gamma-butyrolactone and about 40 vol % of 1,2 dimethoxyethane. With reference to FIGS. 3 and 4 it may be appreciated that, according to the model, battery voltage (mV in FIG. 4 to indicate units of millivolts) is a function of utilization, or depth of discharge (DOD in FIG. 3 and % U in FIG. 4) and current drain, which is expressed in micro amps (μA) in FIG. 3, and as average current density, j (current divided by cathode area, which denoted as "A" in the exemplary code presented below), in the equation of FIG. 4. The model was empirically derived according to discharge data (voltage, millivolts, versus capacity, milliamp hours, for average current drains of 10, 20, 40, 80, 160, 320 and 640 μA) collected from the discharge testing of a group of hybrid cathode battery cells having the exemplary chemistry defined above. The model, being composed of a continuous function that is the sum of four sigmoids and an inverse linear function, defines mean performance over a range of current densities between about 2 μA/cm$^2$ and about 120 μA/cm$^2$, and is valid for 8:1 hybrid cathode medium-rate design batteries which include cathodes having a thickness of about 0.2635 cm. The remaining values for a's, b's, c's and d's in the equation of FIG. 4 are constants describing a linear dependence on the natural log (ln) of current density, j, wherein 's' and 'i' stand for slope and intercept, respectively. According to the exemplary battery described above, the constants have the following values:

| | | |
|---|---|---|
| a1i = 1539.638808 | | a3s = −68.2329044 |
| a1s = 96.51332057 | | b3i = 111.2942791 |
| b1i = 263.2151899 | | b3s = −8.397220729 |
| b1s = 45.95491553 | | c3i = −17.4660755 |
| c1i = 99.79527187 | | c3s = 0.371829129 |
| c1s = −0.763492632 | | a4i = 513.8243731 |
| d1i = −0.80075693 | | a4s = −105.4823468 |
| d1s = −0.147524143 | | b4i = 137.4776252 |
| a2i = 178.5774773 | | b4s = −10.57044628 |
| a2s = −16.76898322 | | c4i = −34.14648953 |
| b2i = 91.57887975 | | c4s = 8.214314006 |
| b2s = −2.012539503 | | a5i = 0.005599606 |
| c2i = −0.877895093 | | a5s = −0.00058946 |
| c2s = −0.327193718 | | b5i = 0.006570709 |
| a3i = 579.5959788 | | b5s = 0.0000958809 |

The depth of discharge (DOD) is defined as discharged capacity, $\Delta Q$, divided by the initial capacity, $Q_{max}$ of the battery (multiplied by 100 for a percentage), and a simplified expression of battery voltage is as follows:

$$V = f(\Delta Q, I),$$

wherein I is current drain. An average current drain may be expressed as $$I_{avg} = \Delta Q / \Delta t,$$

wherein $\Delta t$ is elapsed time. Thus, it may be appreciated that, given an initial current drain of the battery, prior to commencement of battery service at implant, given the initial capacity of the battery, and given a measured battery voltage at tracked points in time, during battery service, iterative calculations and/or determinations of battery voltage at each tracked point in time, per the equation shown in FIG. 4, may be performed, wherein an estimated average current drain (evolved at each subsequent point in time from the initial current drain) is incremented until the calculated voltage converges on the measured voltage at each tracked point in time. With reference to the plot of FIG. 3, given the time of a particular voltage measurement, there is a single DOD value, for a given average current drain, that will yield the measured battery voltage. The Visual Basic code of a "root-finder" algorithm, which includes the above described iterative calculation and/or determination, for carrying out methods of the present invention.

```
Function DOD3(V As Double, dt As Double, DODlast As Double,
Ilast As Double) As
Double
Dim Iest As Double, Imax As Double, Imin As Double, Vcalc
As Double, dQest As
Double Dim DODest As Double
Qmax = 1327
A = 4.522
Iest = Ilast + 0.000001
Imax = 0.09
Imin = 0.005
Qlast = DODlast * Qmax / 100
n = 0
Do
    n = n + 1
    dQest = Iest * dt
    DODest = 100 * (Qlast + dQest) / Qmax
    Vcalc = mV(Iest * 1000 / A, DODest) / 1000
    If Vcalc > V Then
        Imin = Iest
        Iest = 0.5 * (Imax + Iest)
    Else
        Imax = Iest
        Iest = 0.5 * (Imin + Iest)
    End If
Loop Until ((Abs(Vcalc − V) < 0.0001) Or ((Imax − Iest) < 0.0001 *
Imax) Or (n = 1000))
If n = 100 Then
    DOD3 = DODlast
Else
```

```
    DOD3 = DODest
End If
End Function
```

The above algorithm uses the bisection method, but alternate "root finder" algorithms, for example, using Newton's method or the secant method, may be employed by embodiments of the present invention.

Figure 5:
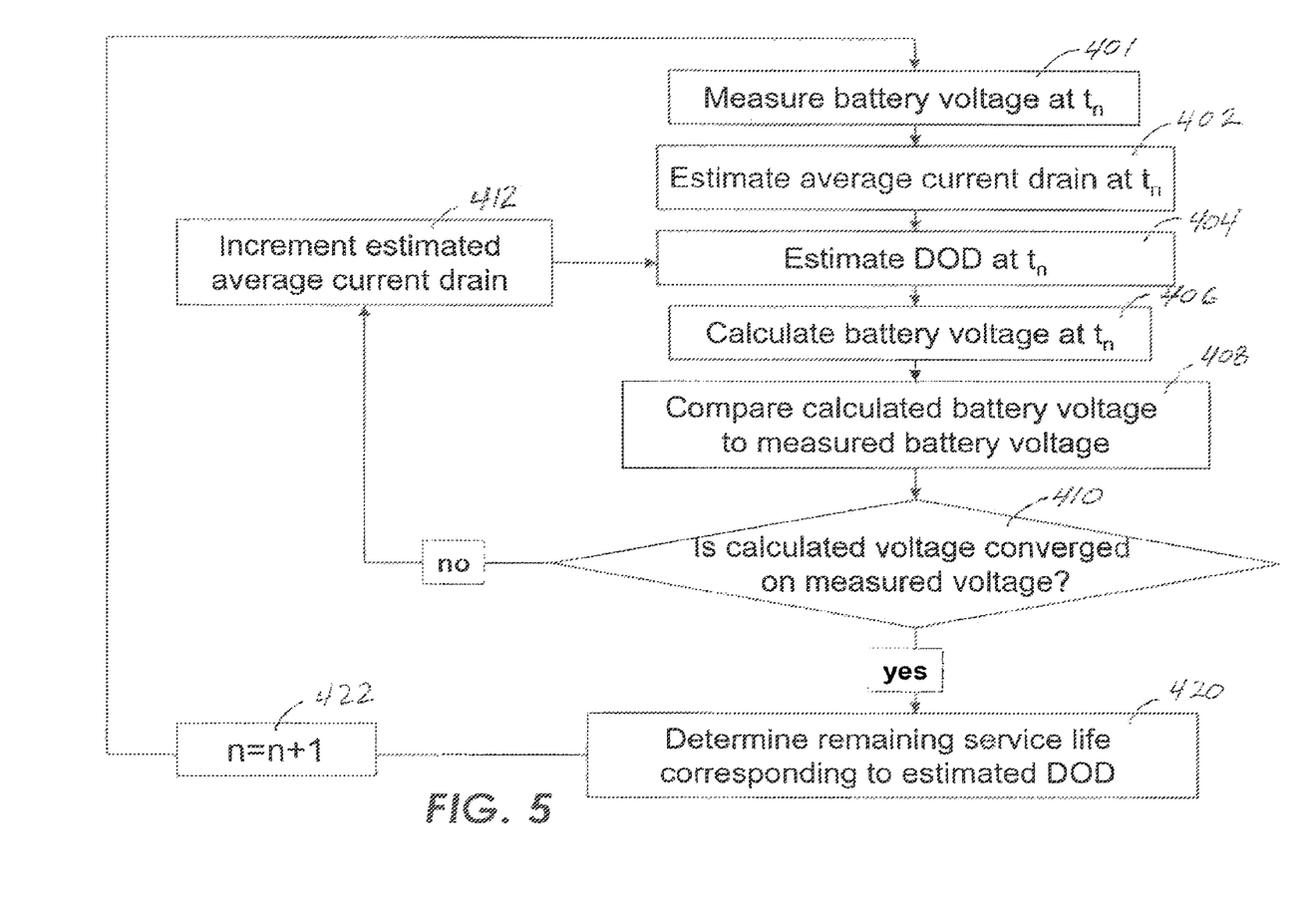
FIG. 5 is a flow diagram that depicts estimating remaining battery service life in an implantable medical device.

FIG. 5 is a flow diagram that depicts estimating remaining battery service life in an implantable medical device. Blocks 402, 404, 406, 408, 410 and 412 of FIG. 5 correspond to the exemplary algorithm detailed in the above code, wherein iterative calculations are performed by incrementing an estimated average current drain (Iest), per block 412, and estimating a corresponding DOD (DODest), per block 404, until a difference between the calculated battery voltage (Vcalc), per block 406, and the measured battery voltage (V), per block 401, is small enough (e.g. less than about 0.0001 volt, per the code) to affirm that Vcalc is converged on V at block 410. At each subsequent point in time, represented by block 422, when a voltage measurement is taken, per block 401, the iterative calculation starts with the incremented estimate of average current drain that corresponds to the converged calculated voltage at the preceding point in time (Ilast). Although not detailed in the chart, the above code instructs that Ilast be initially incremented by 0.000001 milliamp (0.001 µA) for the start of each iterative calculation. Thus, each iterative calculation and/or determination initially uses the final incremented estimated average current drain from the previous iterative calculation. Battery voltage measurements for iterative calculations may be individual measurements scheduled at any time increment, or, preferably averages of measurements taken over intervals, either consistent or variable, ranging from about two weeks to about 10 weeks. Individual voltage measurements may constitute a daily average of multiple measurements, for example, eight measurements, over a day. As previously described, the battery voltage measurements may be stored in IMD 12 (FIGS. 1-2) until a time of a scheduled patient check up, when a telemetry link is established to uplink the voltage measurements and associated points in time to external device 26 where the iterative calculation is performed for each point in time.

According to alternate methods of the present invention, a discharge model, for example, the equation shown in FIG. 4, may be re-arranged to define current as a function of voltage and time, so that the above described iterative calculations are not required, and a DOD may be estimated based on average current drain calculated directly from measured voltage the corresponding elapsed amount of time. Furthermore, battery chemistry impacted by temperature variation, a temperature-corrected discharge model may be employed. Therefore, in this embodiment, temperature and voltage are also measured.

FIG. 5 further illustrates block 420 in which a remaining service life, which corresponds to the last estimated DOD, is determined. The remaining service life, according to preferred embodiments of the present invention, is defined as the time remaining before a start of a period of time known as the recommended replacement time (RRT). the RRT provides a safety factor to assure that the battery will not become completely depleted (100% DOD) prior to the patient and/or clinician receiving a signal or warning that the battery life is nearing an end, sometimes called an end of life (EOL) indicator. According to some embodiments of the present invention, a DOD of less than 100% and greater than about 85% corresponds to a time when an EOL indicator is provided, for example via an audible signal emitted, for example, from a transducer 128 of IMD 12, shown in FIG. 2 or via a report generated by external device 26 during a telemetry session between IMD 12 and external device 26.

FIG. 6 is a chart including an exemplary array of times, in units of months, remaining before the start of the RRT for each DOD listed along the left hand side of the array. The times, otherwise known as longevity predictions, were derived using the discharge model equation of FIG. 4, wherein voltage was calculated at 0.5% increments of DOD, for each of the current drains listed across the top of the array. The times, or longevity predictions, associated with each current drain and the increments of DOD included in the chart, were calculated from the discharge model using a battery voltage of about 2.6 volts for the start of RRT. Referring back to FIG. 3, it can be seen that 2.6 volts about corresponds with the increasingly rapid decline in battery voltage toward the end of the life of the battery, where the start of RRT is preferably defined. It should be noted that the discharge curves of FIG. 3 are for the exemplary battery chemistry, previously defined, and any voltage value corresponding to a relatively steep part of the discharge curve near the end of life could be selected. Because of sources of variability associated with deriving these longevity predictions, the predictions are given in terms of minimum and maximum values, which correspond to 5% and 95% confidence limits, respectively, for example, calculated via Monte Carlo simulations using normal distributions of cathode mass and battery cell voltage, and using a uniform distribution for error in voltage readings. According to certain embodiments of the present invention, a chart including an array, similar to that illustrated in FIG. 6, is programmed, preferably into external device 26, along with instructions for determining the remaining battery service life, i.e. time to RRT. By referencing the array with the last incremented estimated current drain (block 412 of FIG. 5) and the last estimated DOD (block 404 of FIG. 5), which resulted in a converged calculated voltage (block 410 of FIG. 5), and using interpolation, if necessary, the time to RRT may be determined to be within the corresponding range defined by the chart.

Figure 7:
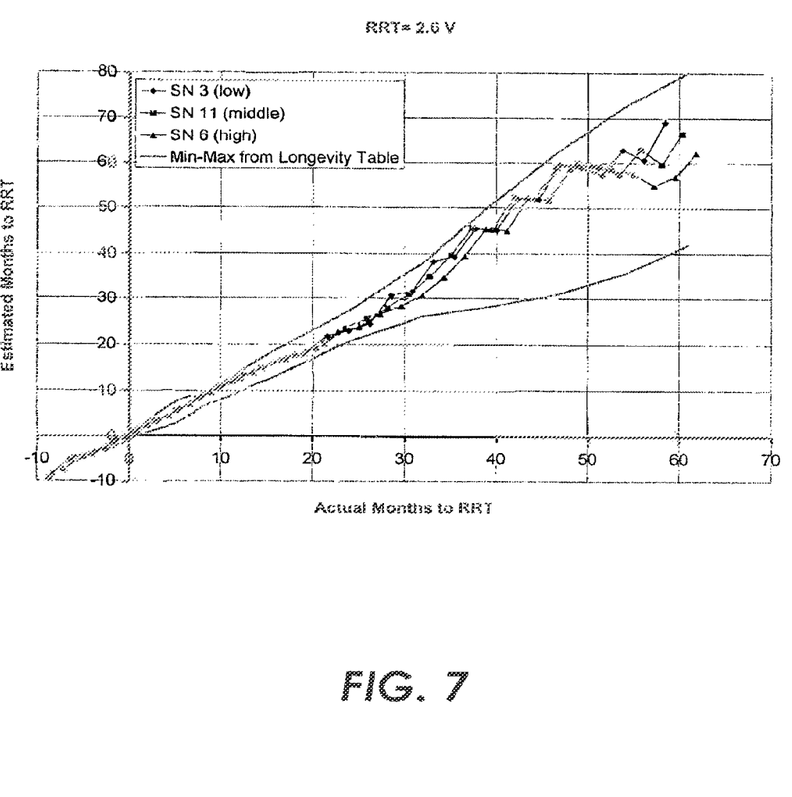
FIG. 7 is an exemplary plot depicting an accuracy of exemplary longevity predictions made according to some methods of the present invention.

FIG. 7 is a plot depicting an accuracy of exemplary battery longevity predictions made according to some methods of the present invention. Values of predicted months, determined via the methods described herein, versus actual measured months to the start of RRT (battery voltage of 2.6 volts at start of RRT) are plotted for two life test battery samples, SN 3, SN 11 and SN 6. The samples were discharged on a constant 86.6 ohm load so that the current drain declined as the battery voltage declined. Although future current drain may change, the methods incorporate an assumption that the most recent estimated average current drain will continue into the future. However, with reference to FIG. 7, it may be appreciated that the predictions are generally conservative, estimating a fewer number of months to the start of RRT, and that the predictions become more accurate as the battery comes closer to complete depletion (100% DOD), where the slope of the characteristic discharge curves (FIG. 3) becomes steeper.

Figure 8:
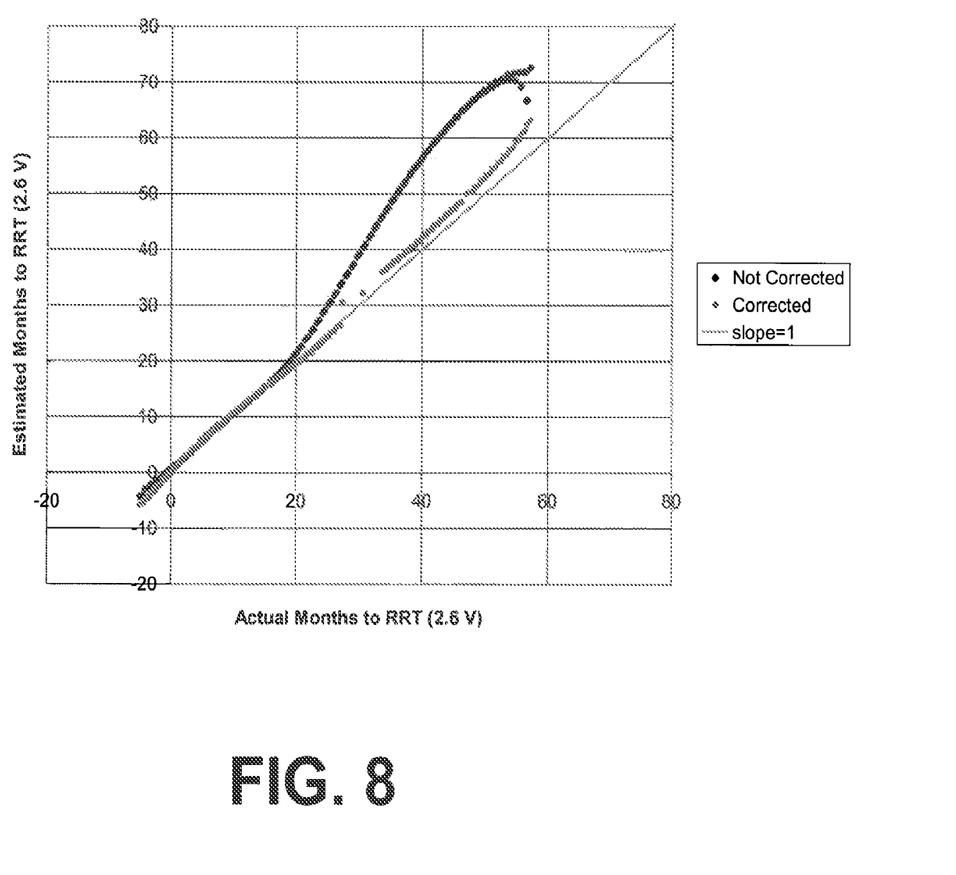
FIG. 8 graphically compares estimation of the longevity of a battery based upon a longevity estimator algorithm to a modified longevity estimator algorithm.

FIG. 8 depicts another embodiment that takes into account periodic episodes of high current drain (e.g. 3-10 Ampere (A) for an implantable cardioverter defibrillator (ICD) when estimating battery longevity. In this embodiment, the longevity estimator algorithm, as described above, is modified. The modified longevity estimator algorithm addresses periodic episodes of high current drain that typically occurs with charging of the high energy capacitors. High energy capacitors store the energy needed to deliver high voltage (e.g. 1-40 joules) for cardioversion therapy and/or defibrillation therapy for an implantable medical device (IMD) such as an ICD. The modified longevity estimator algorithm, described below, may also be used in IMDs with episodes of not-so-high current drain (e.g. less than 1-50 milliamperes (mA) etc.) and/or that implement Telemetry C that may be involved in high-current applications.

The modified longevity estimator algorithm addresses periodic voltage measurements or determinations performed over a period time in which a high current drain is missed. For example, a battery voltage measurement or determination may be taken every three hours. In one embodiment, the battery voltage measurement may be averaged over a certain time period (e.g. over 48 hours etc.), and then averaged a second time over a specified period (e.g. a two-week period). The high energy capacitors in an IMD may be periodically charged during this period thereby affecting the longevity of the battery. Exemplary periods when charging of the high energy capacitors occurs include delivery of therapy, checking of the charging system during a visit to the doctor, or reformation. During charging of the high energy capacitors, the battery voltage is depressed for the duration of the charge (about 8 seconds), and after the charge, the battery substantially recovers within about 10 seconds. The brief period of voltage depression may be missed when the voltage is sampled, for example, every 3 hours. Accordingly, the average voltage under these circumstances will only reflect the background current drain. The background current drain is the current drain that occurs during on-going operations such as low power processes (e.g. sensing, pacing therapy, current drains due to computations, and any other current drain that maintains the microcomputer-based system 102 of the IMD).

Charging the high energy capacitors removes a significant amount of capacity from the battery, typically about 6 milliamp-hours, which would be about 0.5% of the battery capacity (in a battery with a capacity of 1200 milliamp-hours, for example). The previously described longevity estimator may underestimate the discharged capacity in this case, because the discharged capacity is not reflected by the average voltage measurement.

Referring to FIG. 8, a comparison is made of the longevity estimates with and without the correction for capacity delivered during charging of the high energy capacitors. As shown, a charge occurs every four weeks. The capacity is corrected simply by adding the typical percent of capacity used for charging of the high energy capacitors. In this case, 0.6% of DOD for each charge was used. This is a very simple method that works well, because in this case the % DOD using for a charge does not change very much. In some cases the correction may be more complicated. In the more complicated case, the % DOD is modeled using per charge as a function of battery capacity. (If the % DOD used for a charge varies a lot as a function of depth-of-discharge it may be necessary to use a function of % DOD per charge versus DOD.

To implement the modified longevity estimator algorithm, the Visual Basic module is shown below. The only change is the addition of the term "pDOD*PulseNum." Percent of DOD (pDOD) is used as the pulse correction. PulseNum is the number of full-energy pulses delivered in the most recent period of voltage averaging, which in this case is two weeks. An ICD such as Concerto model no. C154DWK by Medtronic is configured to track PulseNum.

In another embodiment, it may also be useful to average the most recent longevity estimate with one or more previous estimates if a charge occurred during the most recent two-week averaging period. Since the average current drain is much higher when a charge occurs, and charges typically occur less often than two weeks, the longevity estimate will probably be too short. Averaging with one or more previous estimates moderates this effect.

```
Function DOD4(V As Double, dt As Double, DODlast As Double,
Ilast As Double) As
Double
Dim Iest As Double, Imax As Double, Imin As Double,
Vcalc As Double, dQest As
Double
Dim DODest As Double, pDOD As Double, Pulse As Integer
Qmax = 1327
A = 4.522
Iest = Ilast + 0.000001
Imax = 0.1
Imin = 0.005
Qlast = DODlast * Qmax / 100
n = 0
pDOD = 0.6
PulseNum = I
Do
    n = n + 1
    dQest = Iest * dt
    DODest = pDOD * PulseNum + 100 * (Qlast + dQest) / Qmax
    Vcalc = mV(Iest * 1000 / A, DODest) / 1000
    If Vcalc > V Then
        Imin = Iest
        Iest = 0.5 * (Imax + Iest)
    Else
        Imax = Iest
        Iest = 0.5 * (Imin + Iest)
    End If
Loop Until ((Abs(Vcalc – V) < 0.0001) Or ((Imax – Iest) < 0.0001 *
Imax) Or (n = 1000))
If n = 1000 Then
    DOD4 = DODlast
Else
    DOD4 = DODest
End If
End Function
```

In the foregoing detailed description, the invention has been described with reference to specific embodiments. However, it may be appreciated that various modifications and changes can be made without departing from the scope of the invention as set forth in the appended claims. For example, although examples have been provided herein for a particular battery type and associated cathode discharge model, it should be recognized that systems and methods of the present invention may be employed for any battery type for which voltage can be modeled as a function of current drain and DOD.

We claim:

1. A system comprising an implantable medical device and a non-transitory computer readable medium programmed with instructions for executing a method to estimate a remaining service life of a battery of the implantable medical device, the battery having a known initial capacity and a known characteristic discharge model, the discharge model defining battery voltage as a function of an average current drain and discharged capacity, the method comprising:
    tracking time;
    determining battery voltage at least one point in time;
    estimating an average current drain corresponding to the at least one point in time of the battery voltage measurement, the estimated average current drain based upon an incremented initial current drain, the initial current drain being characteristic of the battery prior to a start of service;
    estimating a depth of discharged capacity based on the estimated average current drain, the known initial capacity and the time of the at least one point in time;

iteratively determining battery voltage until the calculated voltage converges on the battery voltage measured at the at least one point in time, wherein each iterative calculation is based on the characteristic discharge model, and wherein each subsequent iteration of the iterative calculation is further based on an incremented estimated depth of discharged capacity and a corresponding incremented estimated average current drain, each incremented estimated average current drain being based upon a difference between a previously calculated voltage of the iterative calculation and the measured voltage; and determining an estimated time of remaining battery service life according to the incremented estimated depth of discharged capacity that corresponds to the converged calculated battery voltage and the corresponding incremented estimated average current drain.

2. The system of claim 1, wherein the at least one point in time comprises a plurality of points in time, and the measured battery voltage corresponds to an average of battery voltage measurements, each measurement being made at one of each of the plurality of points in time.

3. The system of claim 2, wherein the plurality of points in time are spread over one day.

4. The system of claim 2, wherein the plurality of points in time are spread over about fourteen days.

5. The system of claim 2, wherein the plurality of points in time are spread over about seventy days.

6. The system of claim 1, wherein the method further comprises storing each measured battery voltage.

7. The system of claim 1, wherein the method further comprises providing a signal when the incremented estimated depth of discharged capacity that corresponds to the converged calculated battery voltage is about 85% of the initial capacity.

8. The system of claim 1, wherein: the non-transitory computer readable medium is further programmed with an array of a plurality of times of remaining battery service life, each time of the array for a particular estimated average current drain and a particular depth of discharged capacity; and the operation of determining the estimated time of remaining battery service life comprises referencing the array.

9. The system of claim 1, further comprising:
an external device coupled to the implanted device via a telemetry communication link; and wherein a first portion of the non-transitory computer readable medium is included in the implanted device and is programmed with instructions for the operations of tracking time and measuring battery voltage;
a second portion of the non-transitory computer readable medium is included in the external device and is programmed with instructions for the operations of estimating the average current drain, estimating the depth of discharged capacity, iteratively determining battery voltage, and determining the estimated time of remaining battery service life; and
the telemetry communication link transfers tracked times and measured battery voltages to the external device.

10. The system of claim 9, wherein the method further comprises storing each battery voltage measurement, the first portion of the non-transitory computer readable medium being programmed with instructions for the storing operation.

11. The system of claim 9, wherein: the second portion of the non-transitory computer readable medium is further programmed with an array of a plurality of times of remaining battery service life, each time of the array for a particular estimated average current drain and a particular depth of discharged capacity; and the operation of determining the estimated time of remaining battery service life comprises referencing the array.

12. A computer-implemented method for estimating a remaining service life of a battery of an implantable medical device, the battery having a known initial capacity and a known characteristic discharge model, the discharge model defining battery voltage as a function of an average current drain and discharged capacity, and the method comprising:
tracking time;
measuring battery voltage at least one point in time; estimating an average current drain corresponding to the at least one point in time of the battery voltage measurement, the estimated average current drain based upon an incremented initial current drain, the initial current drain being characteristic of the battery prior to a start of service;
estimating a depth of discharged capacity based on the estimated average current drain, the known initial capacity and the time of the at least one point in time;
iteratively determining battery voltage until the calculated voltage converges on the battery voltage measured at the at least one point in time, wherein each iterative calculation is based on the characteristic discharge model, and wherein each subsequent iteration of the iterative calculation is further based on an incremented estimated depth of discharged capacity and a corresponding incremented estimated average current drain, each incremented estimated average current drain being based upon a difference between a previously calculated voltage of the iterative calculation and the measured voltage; and
determining an estimated time of remaining battery service life according to the incremented estimated depth of discharged capacity that corresponds to the converged calculated battery voltage and the corresponding incremented estimated average current drain.

13. The method of claim 12, wherein the at least one point in time comprises a plurality of points in time, and the measured battery voltage corresponds to an average of battery voltage measurements, each measurement at one of each of the plurality of points in time.

14. The method of claim 13, wherein the plurality of points in time are spread over about one day.

15. The method of claim 13, wherein the plurality of points in time are spread over about fourteen days.

16. The method of claim 13, wherein the plurality of points in time are spread over about seventy days.

17. The method of claim 12, further comprising: storing each measured battery voltage in a buffer of the implantable device; establishing a communications link between the implantable medical device and an external device; and transferring the tracked times and each measured battery voltage from the buffer to the external device for the operations of estimating the average current drain, estimating the depth of discharged capacity, iteratively determining battery voltage, and determining the estimated time of remaining battery service life.

18. The method of claim 12, further comprising providing a signal when the incremented estimated depth of discharged capacity that corresponds to the converged calculated battery voltage is about 85% of the initial capacity.

19. The method of claim 12, wherein the operation of determining the estimated time of remaining battery service life comprises referencing an array of a plurality of times of remaining battery service life, each time of the array for a particular estimated average current drain and a particular depth of discharged capacity.

20. A system comprising an implantable medical device and a non-transitory computer readable medium programmed with instructions for executing a method to estimate a remaining service life of a battery of the implantable medical device, the battery having a known initial capacity and a known characteristic discharge model, the discharge model defining battery voltage as a function of an average current drain and discharged capacity, the method comprising:
tracking time;
measuring battery voltage at least one point in time;
determining an average current drain from each measured battery voltage and the corresponding elapsed time of the measurement point in time;
estimating a depth of discharged capacity based on the determined average current drain, the known initial capacity and the elapsed time of the measurement point in time;
iteratively determining battery voltage until the battery voltage converges on the battery voltage measured at the at least one point in time, wherein each iterative calculation is based on the characteristic discharge model, and wherein each subsequent iteration of the iterative calculation is further based on an incremented estimated depth of discharged capacity and a corresponding incremented estimated average current drain, each incremented estimated average current drain being based upon a difference between a previously determined battery voltage of the iterative calculation and the measured battery voltage; and
determining an estimated time of remaining battery service life according to the estimated depth of discharged capacity that corresponds to the converged determined battery voltage and the corresponding incremented estimated average current drain.

21. The system of claim 20, wherein the at least one point in time comprises a plurality of points in time, and the measured battery voltage corresponds to an average of battery voltage measurements, each measurement being made at one of each of the plurality of points in time.

22. The system of claim 21, wherein the plurality of points in time are spread over one day.

23. The system of claim 21, wherein the plurality of points in time are spread over about fourteen days.

24. The system of claim 21, wherein the plurality of points in time are spread over about seventy days.

25. The system of claim 20, wherein the method further comprises storing each measured battery voltage.

26. The system of claim 20, wherein the method further comprises providing a signal when the estimated depth of discharged capacity is about 85% of the initial capacity.

27. The system of claim 20, wherein: the non-transitory computer readable medium is further programmed with an array of a plurality of times of remaining battery service life, each time of the array for a particular average current drain and a particular depth of discharged capacity; and the operation of determining the estimated time of remaining battery service life comprises referencing the array.

28. The system of claim 20, further comprising: an external device coupled to the implanted device via a telemetry communication link; and wherein a first portion of the non-transitory computer readable medium is included in the implanted device and is programmed with instructions for the operations of tracking time and measuring battery voltage; a second portion of the non-transitory computer readable medium is included in the external device and is programmed with instructions for the operations of determining the average current drain, estimating the depth of discharged capacity, and determining the estimated time of remaining battery service life; and the telemetry communication link transfers tracked times and measured battery voltages to the external device.

29. The system of claim 28, wherein the method further comprises storing each battery voltage measurement, the first portion of the computer readable medium being programmed with instructions for the storing operation.

30. The system of claim 28, wherein: the second portion of the non-transitory computer readable medium is further programmed with an array of a plurality of times of remaining battery service life, each time of the array for a particular estimated average current drain and a particular depth of discharged capacity; and the operation of determining the estimated time of remaining battery service life comprises referencing the array.

* * * * *